United States Patent [19]
Drainville et al.

[11] Patent Number: 5,374,257
[45] Date of Patent: Dec. 20, 1994

[54] FLUID COLLECTION CHAMBER

[75] Inventors: Nancy Drainville, Attleboro, Mass.; Timothy Appleby, Smithfield; Augustus Felix, Providence, both of R.I.

[73] Assignee: C. R. Bard, Inc., Murray Hill, N.J.

[21] Appl. No.: 73,607

[22] Filed: Jun. 7, 1993

Related U.S. Application Data

[63] Continuation of Ser. No. 856,387, Mar. 23, 1992, abandoned.

[51] Int. Cl.$^5$ ............................................. A61M 5/14
[52] U.S. Cl. .................................. 604/319; 604/4; 604/408; 383/2
[58] Field of Search ............... 128/760, 762, 767, 771, 128/DIG. 4; 604/4, 80, 128, 132, 140, 153, 183, 185, 186, 257, 260, 262, 318, 319, 320, 326, 404–408; 383/2, 35, 41, 119; 222/206, 207, 214; 220/629, 630, 646, 647, 650

[56] References Cited

U.S. PATENT DOCUMENTS

| | | |
|---|---|---|
| 1,971,642 | 4/1933 | Champlin . |
| 2,470,977 | 5/1949 | Chidsey, Jr. . |
| 2,908,463 | 10/1959 | Chenette . |
| 3,211,144 | 10/1965 | Nehring . |
| 3,650,272 | 3/1972 | Ericson . |
| 3,866,608 | 2/1975 | Reynolds et al. . |
| 3,872,868 | 3/1975 | Kline . |
| 3,982,538 | 9/1976 | Sharpe . |
| 4,014,329 | 3/1977 | Welch et al. . |
| 4,126,135 | 11/1978 | Hinman, Jr. . |
| 4,161,179 | 7/1979 | Abramson . |
| 4,295,619 | 10/1981 | Kulin et al. . |
| 4,305,389 | 12/1981 | Potter . |
| 4,312,352 | 1/1982 | Meisch et al. . |
| 4,326,526 | 4/1982 | Buck et al. . |
| 4,393,880 | 7/1983 | Taylor . |
| 4,402,687 | 9/1983 | Denty et al. . |
| 4,424,053 | 1/1984 | Kurtz et al. . |
| 4,443,220 | 4/1984 | Hauer et al. ................. 604/408 |
| 4,449,969 | 5/1984 | Schweizer . |
| 4,500,308 | 2/1985 | Kurtz et al. . |
| 4,501,581 | 2/1985 | Kurtz et al. . |
| 4,501,584 | 2/1985 | Cianci et al. . |
| 4,543,084 | 9/1985 | Bailey . |
| 4,553,970 | 11/1985 | Lewis, Jr. . |
| 4,583,972 | 4/1986 | Hunter, III et al. . |
| 4,637,934 | 1/1987 | White . |
| 4,642,088 | 2/1987 | Gunter . |
| 4,650,478 | 3/1987 | Dunn . |
| 4,664,652 | 5/1987 | Weilbacher . |
| 4,675,011 | 6/1987 | Kurtz et al. . |
| 4,700,871 | 10/1987 | Matsuo et al. . |
| 4,731,072 | 3/1988 | Aid ................................ 604/408 |
| 4,772,256 | 9/1988 | Lane et al. . |
| 4,775,360 | 10/1988 | Lane et al. . |
| 4,781,707 | 11/1988 | Boehringer et al. . |
| 4,798,578 | 1/1989 | Ranford . |
| 4,838,872 | 6/1989 | Sherlock ........................ 604/319 |
| 4,857,042 | 8/1989 | Schneider ........................ 604/4 |
| 4,857,042 | 8/1989 | Schneider . |
| 4,943,288 | 7/1990 | Kurtz et al. ..................... 604/408 |
| 4,955,877 | 9/1990 | Kurtz et al. . |
| 4,973,327 | 11/1990 | Goodrich, Jr. et al. ......... 604/408 |
| 4,976,707 | 12/1990 | Bodicky et al. ................. 604/408 |
| 5,011,470 | 4/1991 | Kurtz et al. ..................... 604/4 |
| 5,025,925 | 6/1991 | Wiklund ......................... 206/386 |
| 5,045,077 | 9/1991 | Blake, III . |
| 5,158,369 | 10/1992 | Derby ............................ 383/67 |

FOREIGN PATENT DOCUMENTS

| | | |
|---|---|---|
| 0080364 | 6/1983 | European Pat. Off. . |
| 0092313 | 10/1983 | European Pat. Off. . |
| 0278770 | 8/1988 | European Pat. Off. . |
| 2421433 | 11/1975 | Germany . |
| 9116861 | 11/1991 | WIPO ............................. 604/408 |

Primary Examiner—Stephen C. Pellegrino
Assistant Examiner—Guy V. Tucker
Attorney, Agent, or Firm—Wolf, Greenfield & Sacks

[57] ABSTRACT

A collapsible and expandable container for collecting fluids under the influence of a vacuum. A rigid front wall and a flexible rear wall define a variable volume collection bag interior. A plurality of rigid, elongated panels are spaced about and attached to the flexible rear wall. A rigid stent is releasably engageable to the panels to distend the rear wall relative to the rigid front wall.

28 Claims, 13 Drawing Sheets

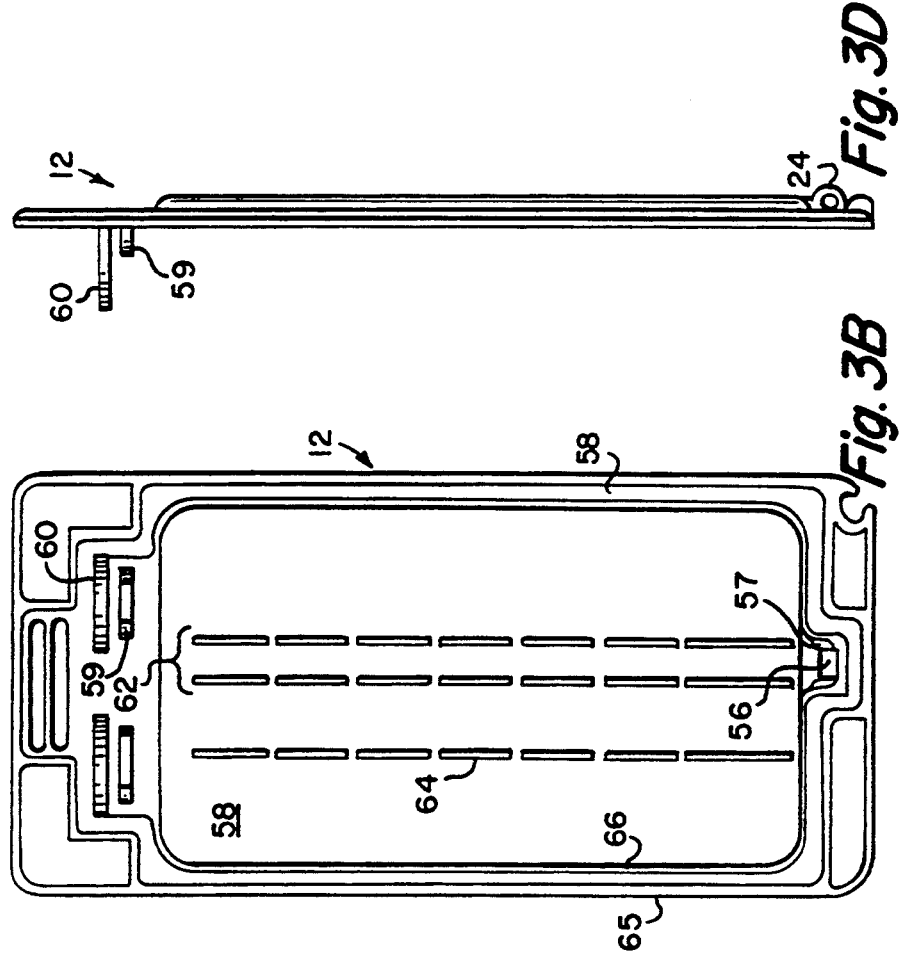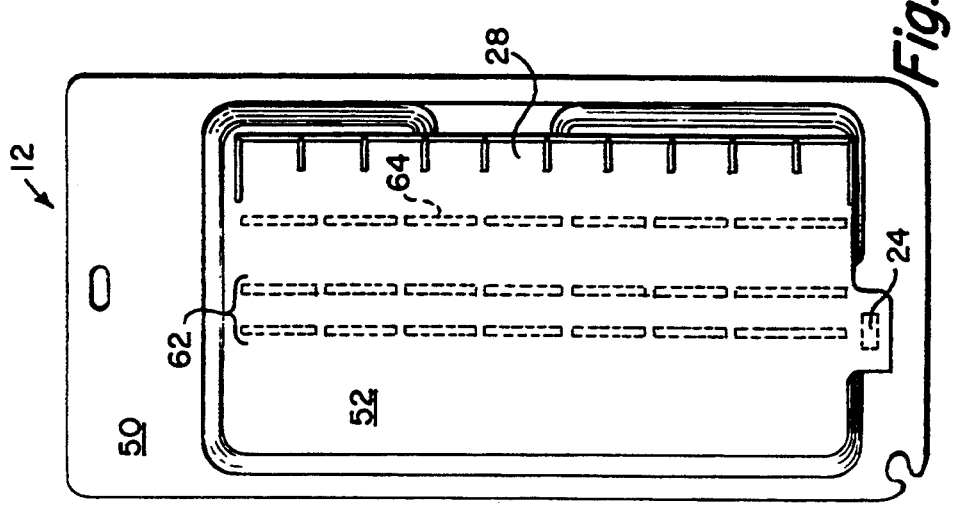

FLUID COLLECTION CHAMBER

This application is a continuation of application Ser. No. 07/856,387, filed Mar. 23, 1992, now abandoned.

FIELD OF INVENTION

The present invention relates to a collapsible and expandable fluid collection container.

BACKGROUND OF THE INVENTION

Various autotransfusion containers which operate under a vacuum to collect blood from a patient during surgery also may be used to reinfuse the collected blood into the patient. Prior art containers traditionally were formed from non-collapsible glass blood collection bottles. The art then evolved to pliable plastic collection bags which, when compressed, would increase the reinfusion flow of the collected liquids.

To prevent the vacuum from collapsing the container, the pliable prior art containers are distended mechanically during the collection procedure. The following patents are representative of such prior art devices. U.S. Pat. No. 4,443,220 discloses the expanding of a cylindrical blood collection bag by engaging a plurality of sleeve-like loops annularly spaced about the collection bag with the elongated tines of a stent. U.S. Pat. No. 4,838,872 discloses a collapsible blood collection bag which is distended by compressing stiffener members connected to the bag. U.S. Pat. No. 4,943,288 discloses a reinfusion bag which is maintained in an open configuration by separating frame members attached to the bag with a pair of crossed-locking arms which extend across the top and bottom of the reinfusion bag.

The prior art also discloses non-mechanical means for holding the collection bag in an open or expanded configuration during the vacuum influenced fluid collection procedure. U.S. Pat. No. 3,866,608 discloses the application of a second vacuum between the surface of the collection bag and a rigid outer container to prevent container collapse. U.S. Pat. No. 4,781,707 discloses a hermetically sealed chamber between a flexible collection bag and an outer container which prevents the collection bag from collapsing during the blood collection process.

These prior art devices have certain disadvantages. The portions of the plastic collection bags which are not directly attached to the mechanical support structure tend to partially collapse when the vacuum is applied to the container interior. Consequently, the volume scale provided on these plastic containers gives an inaccurate measure of the volume of fluids being collected. That discrepancy may prove harmful when a course of treatment is based on the amount of blood loss. The vacuum expanded containers provide a more reliable container volume but are more difficult to operate. Release of the outer vacuum, which is required to allow the inner container to collapse during reinfusion of the collected blood, has proven problematic.

SUMMARY OF THE INVENTION

The present invention relates to a container for collecting body fluids, such as surgically and post-operatively shed blood, under the influence of a vacuum. The container includes a rigid front wall and a flexible rear wall which is collapsible and distendible relative to the rigid front wall. A plurality of rigid flat panels are spaced about and connected to the flexible rear wall and are engageable with a rigid, elongated stent. The interlocked stent and flat panels provide a rigid configuration that prevents the flexible rear wall from collapsing notwithstanding the vacuum applied to the collection container during blood collection. Upon detachment of the stent, the flexible rear wall is again collapsible which allows the autologuus blood to be reinfused to the patient.

It is among the various objects of the present invention to provide a collection container which is distendible and collapsible.

It is another of the various objects of the invention to provide a collection container having a relatively reliable volume when a vacuum is operating on the interior thereof.

Other objects and features of the present invention will become apparent from the following detailed description when taken in connection with the accompanying drawings which disclose multiple embodiments of the invention. It is to be understood that the drawings are designed for the purpose of illustration only and are not intended as a definition of the limits of the invention.

DESCRIPTION OF THE DRAWINGS

The foregoing and other objects and advantages of the invention will be appreciated more fully from the following drawings in which:

FIG. 3A is a front illustration of the rigid front wall in accordance with the invention;

FIG. 3B is a rear illustration of the rigid front wall in accordance with the invention;

FIG. 3C is a top illustration of the rigid front wall in accordance with the invention;

FIG. 3D is a side illustration of the rigid front wall in accordance with the invention;

DESCRIPTION OF THE PREFERRED EMBODIMENTS

Figure 1:
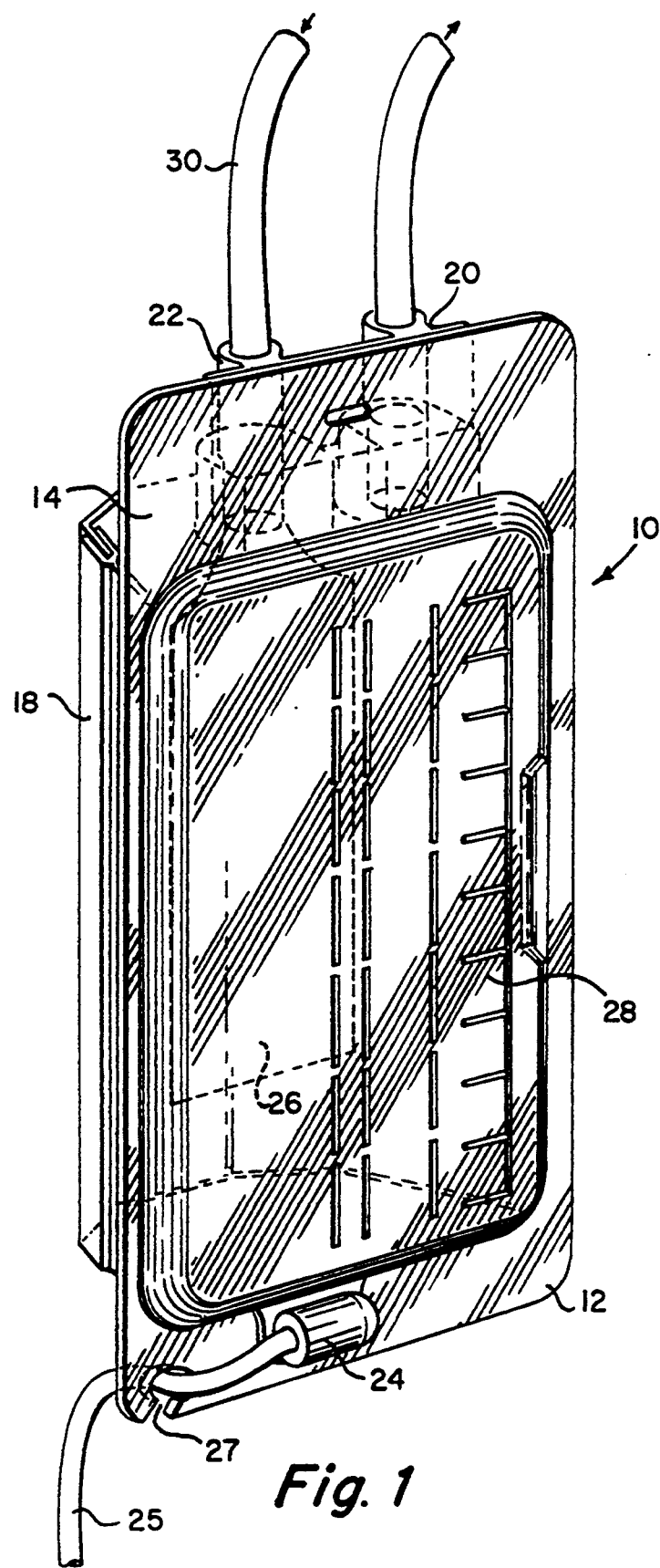
FIG. 1 is a front illustration of the fluid collection container in accordance with the invention.
Figure 2:
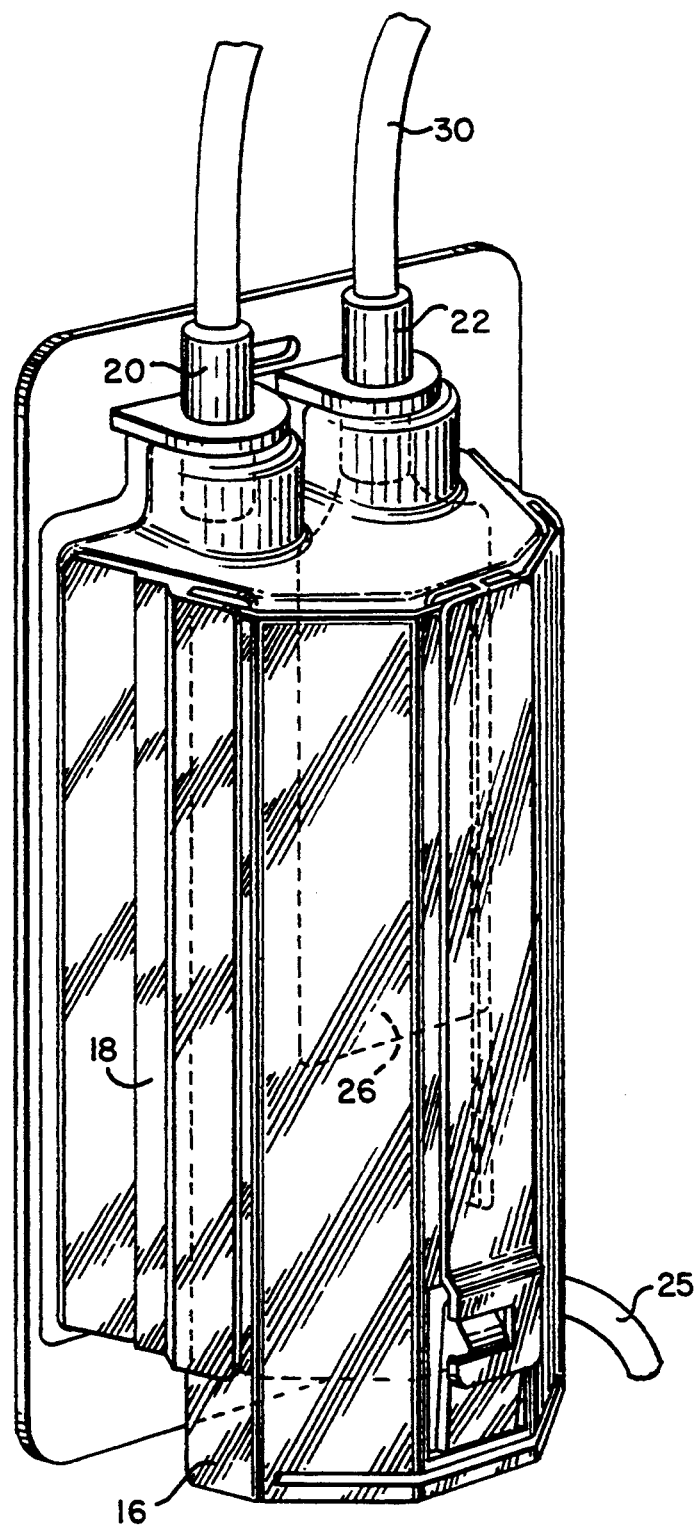
FIG. 2 is a rear illustration of the fluid collection container in accordance with the invention.

The fluid collection container 10 illustrated in FIGS. 1 and 2 includes a rigid front wall 12 and a flexible rear wall 14 which is collapsible and expandable relative to the rigid front wall 12. In the distended configuration, liquid and gaseous fluid from the body cavity or wound being drained flow under the influence of vacuum into the collection container 10. In a collapsed configuration, the flexible rear wall 14 is foldable relative to the rigid front wall 12 to allow the collected liquid fluids to be reinfused to the patient.

The flexible rear wall 14 is held open by interlocking a rigid, elongated stent 16 to a plurality of stent engaging panels 18 attached at spaced locations about the flexible rear wall 14. The interlocked stent 16 and stent engaging panels 18 restrain the flexible rear wall 14 against collapsing under the influence of the vacuum operating on the interior of the collection bag during the collection procedure. To optimize the resistance of the flexible rear wall 14 to the negative pressure in the interior of the container, a substantial portion of the surface of the flexible rear wall 14 is attached directly to the stent engaging panels 18.

After attaching the stent 16 to the stent engaging panels 18, a suction inlet 20 is connected to a source of suction such as the wall outlet of a hospital suction system and a fluid inlet 22 is connected to a drain tube 30 which is placed in communication with the body site being drained. Gas or air, and blood, are drawn from the cavity through the drain tube 30, the fluid inlet 22 and a blood filter 26. The blood filter 26 prevents clots and other semi-solids in the collecting body fluids from being reinfused to the patient. The filter 26 is sealed relative to the fluid inlet 22 to prevent the collecting liquids from shunting directly to the vacuum inlet 20. The filtered blood and other body liquids pass into the bottom of the container. The level of the accumulating liquid is indicated by the volume scale 28 on the transparent or opaque front wall. The collecting gas and air flow through the filter 26 and into the container interior and then are exhausted through the suction inlet 20.

After a sufficient volume of liquid has been collected, the drain tube and suction lines are disconnected. The stent 16 is detached from the stent engaging panels 18 which allows the flexible rear wall 14 to collapse relative to the rigid front wall 12. The closed end of a reinfusion line 25 leading from a reinfusion port 24 in the front wall 12 is spiked by the proximal end of a connecting line (not shown) which may then be connected at a distal end to the patient's circulatory system. Manual or mechanical compression of the flexible rear wall 14 forces the blood and other body fluids from the collection container through the reinfusion line 25 and back to the patient. A slot 27 in the rigid front wall 12 holds the reinfusion line 25 during nonuse. The collection container may be supported above the patient's body so that the fluids are returned to the patient by gravity. Preferably, an adjustable hanger or strap is looped from the rigid front wall 12 over the top of the container 10 to the back of the flexible rear wall and may be attached to a bed rail or an I.V. rack.

The individual components of the collection container will now be explained in greater detail.

The collection bag portion of the container consists of the rigid front wall 12 and the flexible rear wall 14.

The rigid front wall 12 illustrated in FIGS. 3A–D is formed of transparent polycarbonate material, such as Mobay Corp. FCR-2458 or General Electric 124R112 and includes a front face 50 and a rear face 58. The front face 50 includes a belly 52 which contains the graduation scale 28 for measuring the amount of blood accumulating in the collection container 10. The reinfusion port 24 extends from the front wall 12 and is in communication with an opening 56 extending through the lower end of the front wall 12. Preferably, the port 24 is injection molded with the front wall 12. A pair of projections 57 extend perpendicularly from the rear face 58 along opposite edges of the opening 56 and provide support for the portion of the flexible rear wall 14 which defines a reinfusion channel, when the rear wall 14 is attached to the front wall 12.

The rear face 58 includes a rearwardly extending collar 60 which is attached to the suction inlet and the fluid inlet. A pair of flanges 59 are integrally molded to the rear face 58 and include respective U-shaped openings 61 for aligning the suction inlet and the fluid inlet within the container interior. At least one projection, and preferably two rows of rib-shaped projections 62 extend longitudinally along the rear face 58 opposite the rear wall 14, preventing the flexible rear wall from collapsing directly against the front wall which could block blood flow to the reinfusion port during the reinfusion procedure. Alternatively, the rib-shaped projections may extend transversely relative to the axis of the front wall. The rib-shaped projections 62 define a vertical channel for the passage of blood to the front wall opening 56. Vertical spacing of the projections 62 allows transverse blood flow into the channel.

A third row of rib-shaped projections 64 extends longitudinally along the rear side and provides an edge against which a label bearing the volume scale 28 may be aligned. A flat margin 51 surrounds the rear face 58 and is connectable to the margin of the flexible rear wall. The margin 51 is bordered by opposing lips 65,66 which define a shallow recess for holding the ultraviolet activated adhesive used to join the front wall and rear wall together.

Figure 4A:
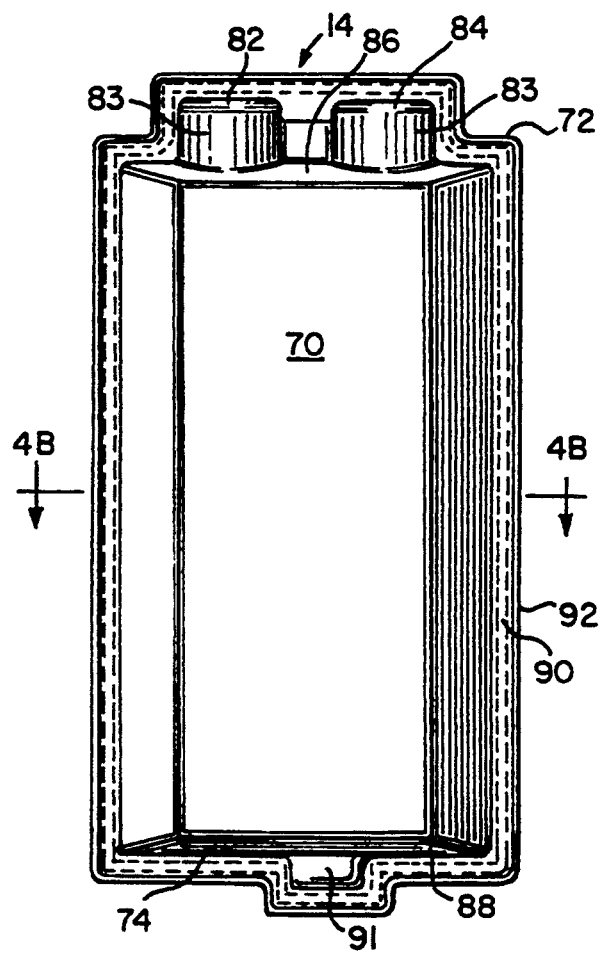
FIG. 4A is a front illustration of the distended configuration of the flexible rear wall.
Figure 4B:
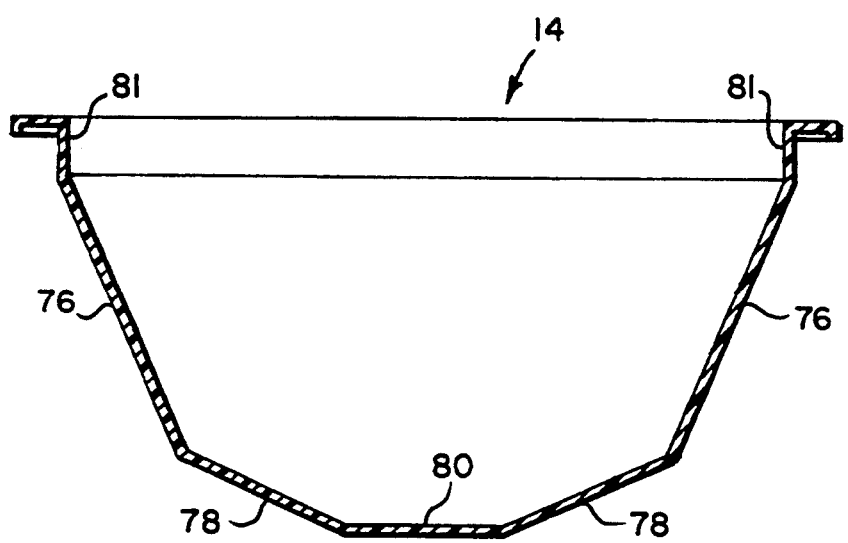
FIG. 4B is a sectional illustration of the distended configuration of the flexible rear wall along line 4B of FIG. 4A.

The flexible rear wall 14 illustrated in FIGS. 4A–B is formed of pliable polyvinyl chloride, such as Regalite 299-998, and includes a main collapsible or intermediate portion 70, a top portion 72 and a lower portion 74. In the distended configuration, the main collapsible portion 70 includes a pair of spaced converging side portions 76, a second pair of spaced converging side portions 78 extending from the first pair 76, and a center portion 80 which extends between the second pair of spaced converging portions 78. The main collapsible portion 70 preferably includes a pair of opposed, parallel lateral portions 81 which further increase the volume of the fully expanded collection container.

The top portion 72 includes a first chamber 82 which is adapted to receive the vacuum inlet 20 and a second chamber 84 which is adapted to receive the fluid inlet 22. The chamber walls 83 surround the distal ends of the vacuum inlet and the fluid inlet preventing inflowing body liquids from shunting directly to the suction inlet 20. The lower portion 74 includes an inclined reinfusion channel 91 which cooperates with the opening 56 in the front wall 12 to form a path into the reinfusion port 24. A flat margin 90 of the flexible rear wall surrounds the main collapsible portion 70, the top portion 72 and the lower portion 74 and includes an upstanding outer edge 92. The edge 92 cooperates with the lips 65,66 of the front wall margin 51 to hold the ultraviolet activated adhesive when the front wall 12 and rear wall 14 are being attached.

Figure 5:
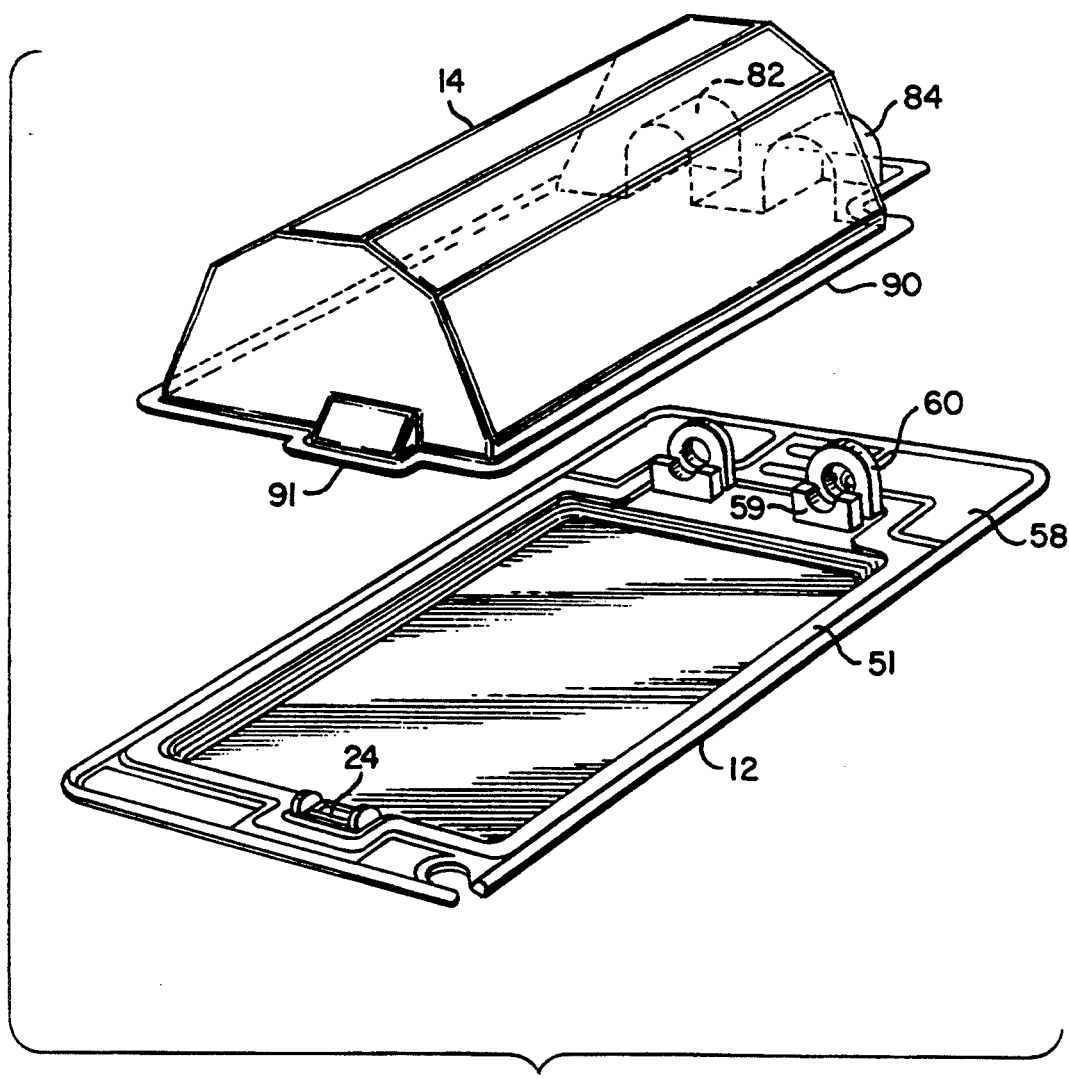
FIG. 5 is an exploded illustration of the assembly of the flexible rear wall and the rigid front wall.

The assembly of the rigid front wall 12 and the flexible rear wall 14 is illustrated in FIG. 5. The flat margin 51 of the rear face 58 of the rigid front wall 12 and the margin 90 of the flexible side wall 14 are aligned to properly position respective interconnecting elements. Thus, the collar 60 is seated on the outer surface of the first and second chambers 82, 84 with the inlet openings in the collar 60 being aligned with the inlet openings in the top wall of the first and second chambers 82, 84. The flanges 59 abut the inner surface of the first and second chambers 82, 84 opposite the collar 60, and the reinfusion channel 91 is positioned adjacent the opening 56 of the reinfusion port 24. The rigid front wall 12 and the flexible rear wall 14 are then joined together, preferably by bonding the flat margin 51 of the rigid front wall 12 and the flat margin 90 of the flexible rear wall with an ultraviolet activated adhesive such as Dymax 20082-M.

Figure 6:
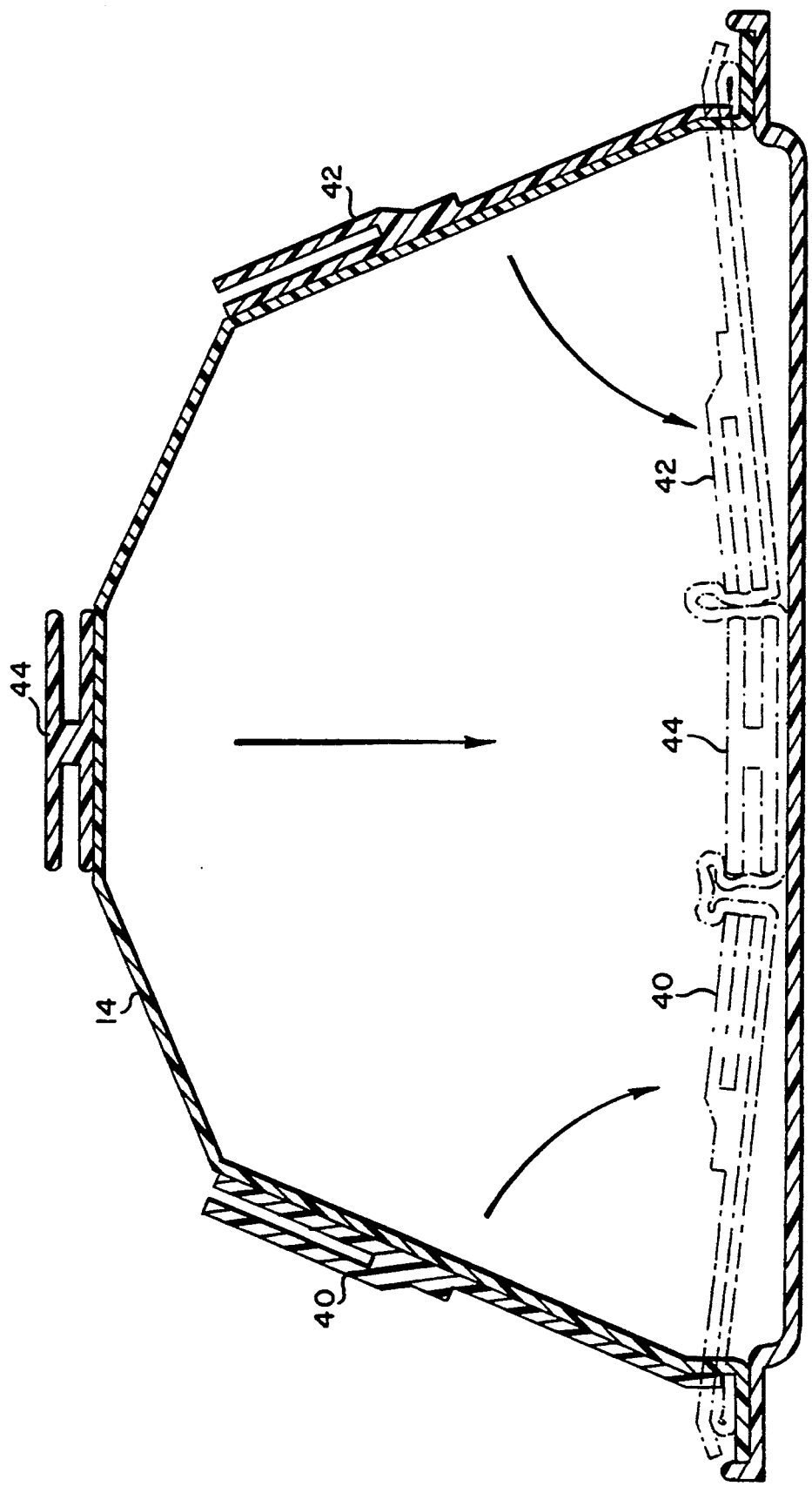
FIG. 6 is a sectional illustration of the device with the stent engaging members in the distended (solid) and collapsed (phantom) configuration.
Figure 7:
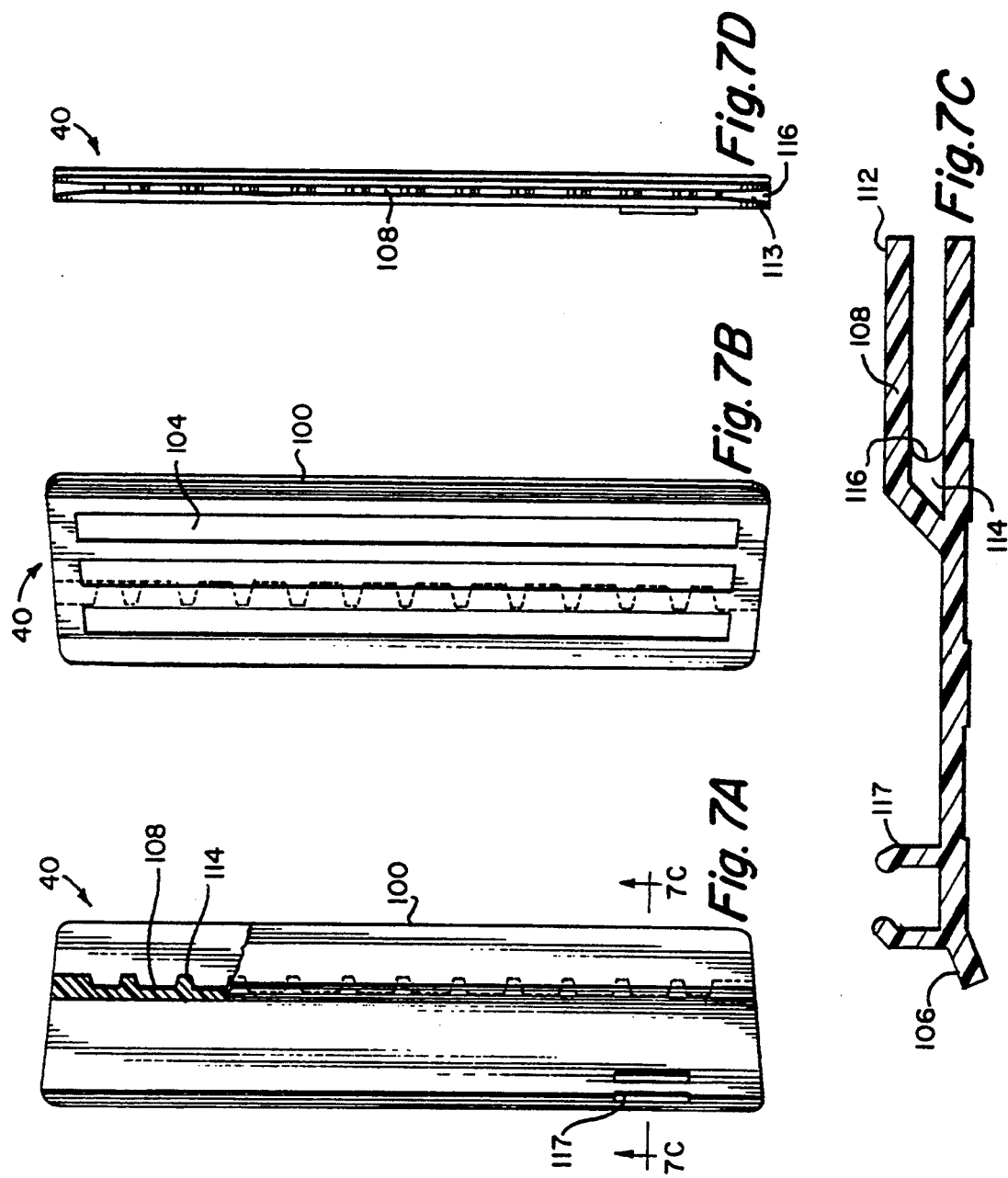
FIG. 7A is a front elevation, partly broken away, of a rear wall panel.
FIG. 7B is a rear elevation of the rear panel of FIG. 7A.
FIG. 7C is a sectional illustration along line 7C of the rear panel illustrated in FIGS. 7A-7B.
FIG. 7D is a side elevation of a rear panel in accordance with the invention.

The interlocking of the stent and stent engaging panels prevents the rear wall from collapsing against the front wall during vacuum collection. The stent engaging panels illustrated in FIGS. 6 include flat side panels 40, 42 and a flat wall panel 44, all of which are bonded to the flexible rear wall 14, preferably with an ultra-violet activated adhesive such as Dymax 20082-M. The side panels 40, 42 and center panel 44 preferably are spaced about the flexible rear wall 14 so that their edges are contiguous when the rear wall is collapsed. The side panels 40, 42 and center panel 44 also preferably have a perimeter coextensive with the perimeter of the respective portions of the rear wall to which they are connected. That arrangement of the panels optimizes the vacuum resisting strength of the rear wall when the stent is interlocked to the panel while still allowing the rear wall robe fully collapsed against the front wall when the stent is detached. As illustrated, the side panels 40, 42 are bonded to the first pair of converging portions of the flexible rear wall and the center panel is bonded to the rear portion of the flexible rear wall.

The side panel 40 illustrated in FIGS. 7A–D includes an elongated main flat body 100 formed of a rigid polycarbonate material such as Mobay Corp. FCR-2458 or General Electric 124R112. A portion 106 of the side panel diverges from the main body 100 and has a perimeter which substantially matches the perimeter of the lateral portion 81 of the fully distended flexible rear wall 14 shown in FIGS. 4A–4B. An elongated flange 108 extends from the main body 100 and defines a stent edge receiving space 110. The inner surface 113 of the flange 108 preferably is flared to facilitate insertion and removal of the stent. A plurality of ribs 114 extend lengthwise along the bottom wall 116 of the flange 108 and help to prevent the side panels 40, 42 from bowing when a vacuum is applied to the fluid collection container 10. A pair of spaced fingers 117 resiliently hold the reinfusion tube or other tubular equipment used with the container. The back of the side panel 40 includes a plurality of elongated recesses 104 which hold the ultraviolet activated adhesive used to join the side panel and the flexible rear wall 14.

Figure 8:
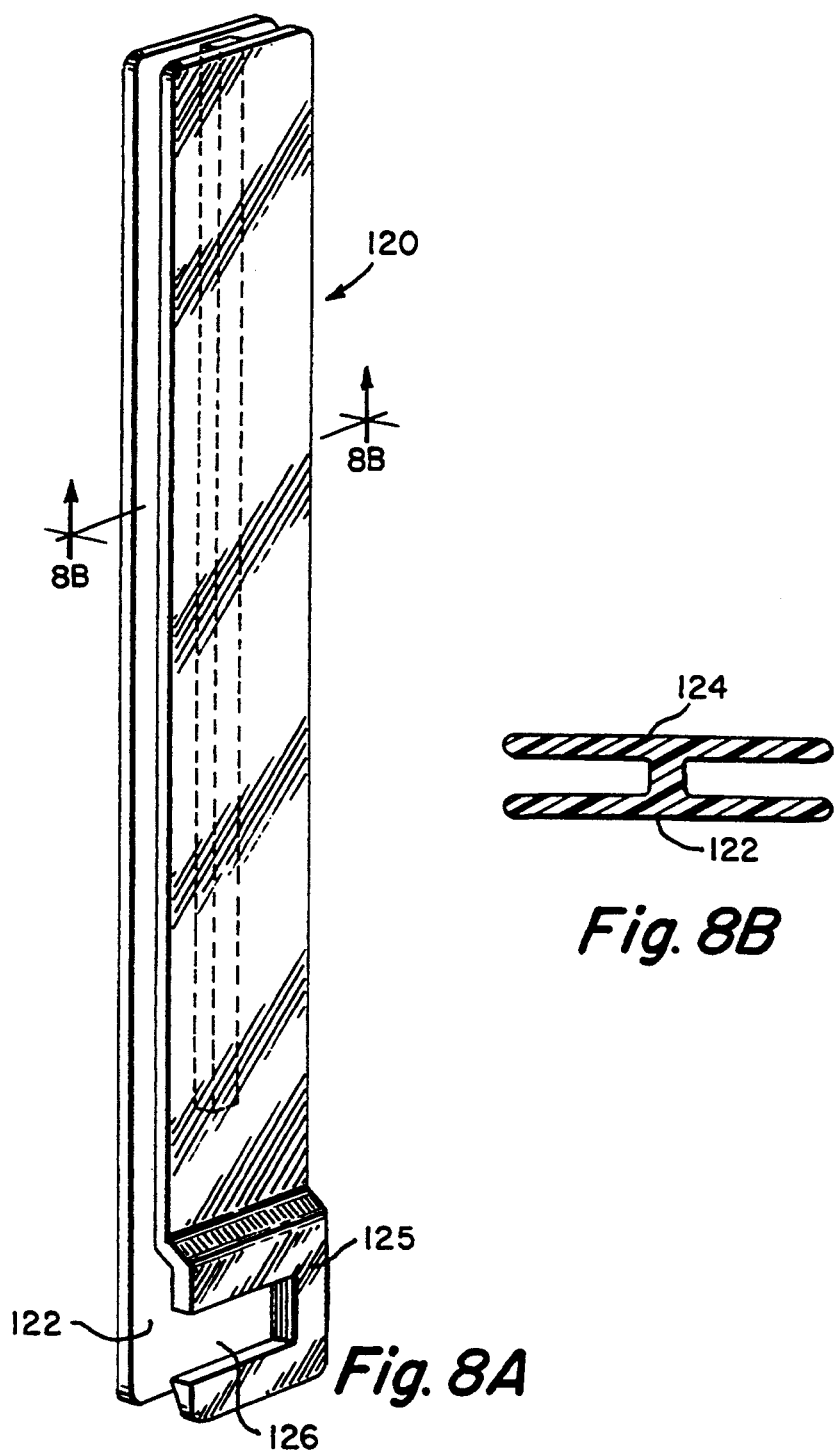
FIG. 8A is a perspective illustration of the center panel.
FIG. 8B is a sectional illustration of the center panel along the line 8B of FIG. 8A.

The center panel 120 illustrated in FIGS. 8A–B includes an elongated main flat body 122 formed of a rigid polycarbonate material such as Mobay Corp. FCR 2458 or General Electric 124R112. A T-shaped flange 124 extends from the elongated main flat body 122 and includes a slot 126 which is adapted to lockingly receive a projection from the stent. The back of the center panel 120 includes an elongated recess for holding an ultraviolet activated adhesive for bonding the center panel to the flexible rear wall.

Figure 9:
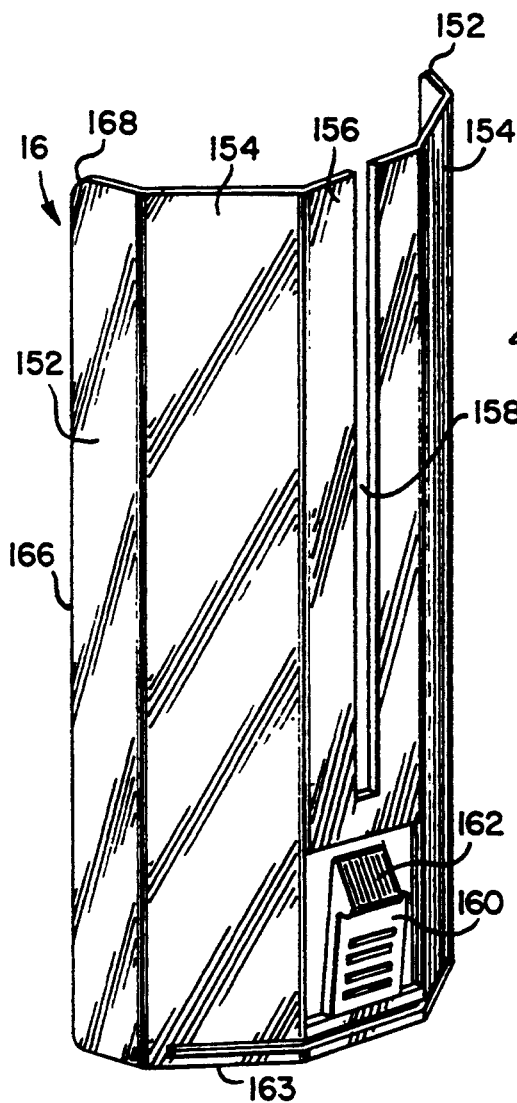
FIG. 9 is a plan illustration of the stent in accordance with the invention.

The rigid, elongated stent 16 illustrated in FIG. 9 is formed of a polycarbonate material such as Mobay Corp. FCR-2458 or General Electric 124R112, and includes a first pair of spaced converging portions 152, a second pair of spaced converging portions 154 extending from the first pair, and a central portion 156 extending between the second pair 154. A slot 158 longitudinally extends along the central portion and slidably receives the T-shaped projection of the center panel. A resilient locking projection 160 extends upwardly from the central region and includes a tapered locking portion 162 which is releasably engageable with the locking slot in the T-shaped flange. A recess 163 surrounds the resilient locking portion 160 and provides an opening into which the locking portion depends when camming against the leading edge of the T-shaped flange, and when depressed by the physician to detach the stent from the central panel. Spaced rib-shaped projections 164 facilitate the depression of the locking portion 160 by the physician. The lateral edges 166 of the stent are sized for slidable movement within the stent receiving space of the side panels. A rounded proximal end 168 promotes insertion of the stent into the stent receiving space.

Figure 10:
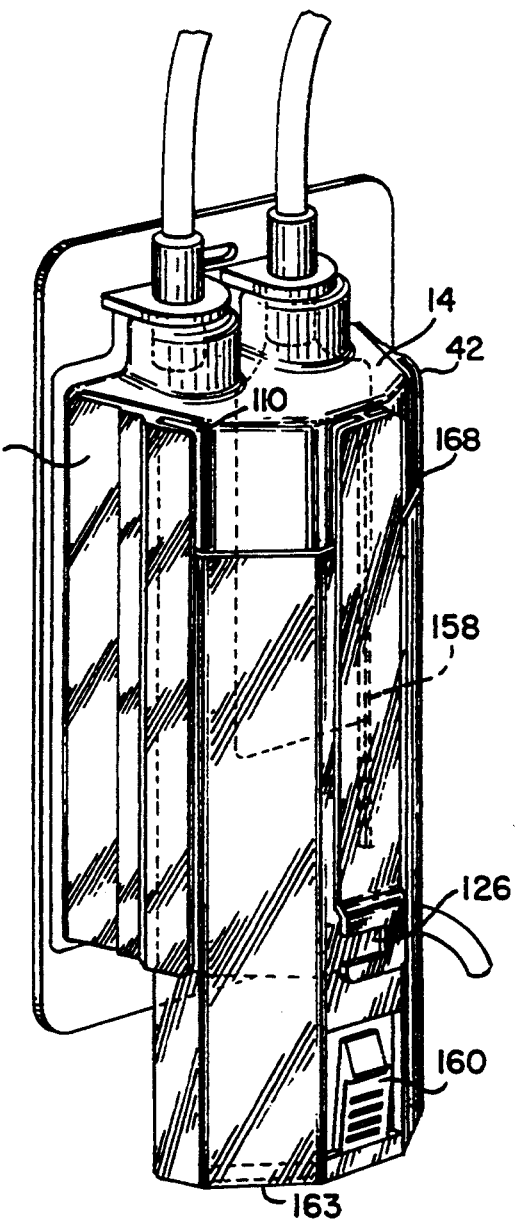
FIG. 10 is an illustration of the attachment of the stent and the stent engaging panels in accordance with the invention.

Attachment of the stent to the stent engaging panels, which maintains the container in the expanded or distended configuration, is illustrated in FIG. 10. The flexible rear wall 14 is manually retracted by pulling the center panel 120 away from the rigid front wall 12. The rounded proximal end 168 of the stent 16 is aligned with the entrance to the stent receiving space 110 and the center slot 158 is aligned with the T-shaped flange of the central panel 120. The stent 16 is advanced until the rounded end 168 reaches the end of the rear panels 40, 42, the T-shaped flange fully mates with the central slot 158 and the locking portion 160 snapped-fits to the locking slot 126. The interlocked stent 16, rear panels 40,42 and center panel 120, rigidify the flexible rear wall 14, preventing the container from collapsing when a vacuum is applied to the container interior. The stent 16 and stent engaging panels 40,42 and 120 are detached by depressing the locking portion 160 and simultaneously withdrawing the stent 16 from the stent receiving spaces 110 and the center panel 120. Once detached, the flexible rear wall 14 is again collapsible relative to the rigid front wall 12 and the collected blood may be reinfused to the patient.

Figure 11:
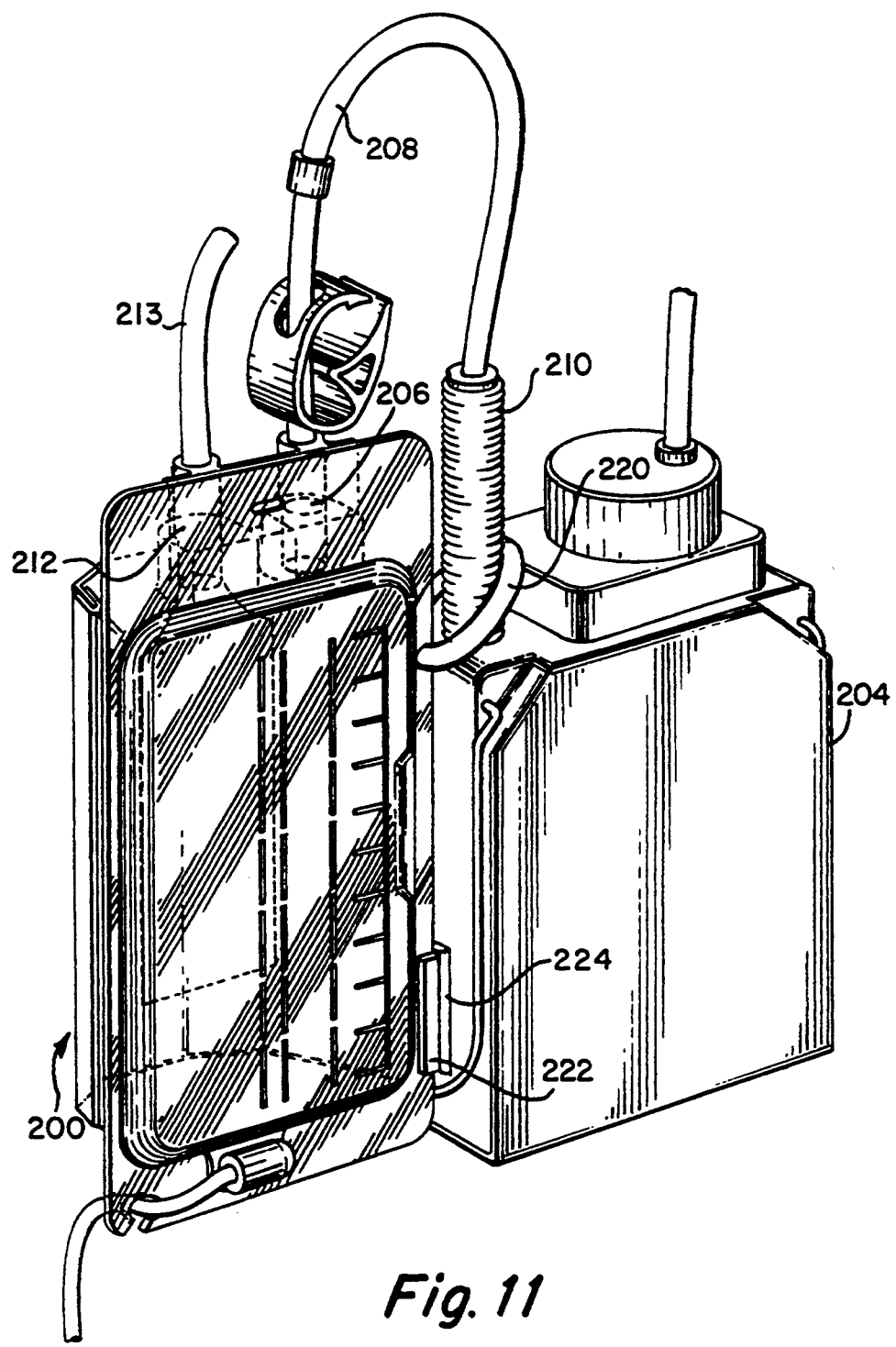
FIG. 11 is an illustration of the fluid collection container mounted to a chest drainage device.

A fluid collection container 200 and chest drainage device 204 assembly is illustrated in FIG. 11. In that arrangement, the level of suction applied to the container may be regulated by the suction regulator provided with the chest drainage device. A suction inlet 206 is connected by a tube 208 to an inlet port 210 of the chest drainage device 204. The fluid inlet 212 of the fluid collection container 200 is connected to a thoracic drain tube 213 which communicates with the pleural cavity of the patient. Suction applied to the chest drainage device 204, which is governed by the regulator (not shown), is correspondingly applied through the tube 208 to the interior of the fluid collection container and to the patient's pleural cavity through the thoracic drain tube 213. The regulated vacuum assists the flow of gas and liquid fluids from the patient's pleural cavity along the thoracic drain tube 213, through the fluid inlet 212 and the depending filter, and into the interior of the fluid collection container 200. The blood and other body fluids accumulate in the fluid collection container 200 while the collecting gases are exhausted through the suction inlet 206, the tube 208, the chest drainage device 204 and ultimately into the hospital suction supply system.

The fluid collection container is detachably connected to the chest drainage device by a hook 220 and a stabilizer flange 222. The hook 220 extends from the top of the side panel and wraps around the tube 208. The stabilizer flange 222 extends from the same side wall panel and abuts a compatible stabilizer flange 224 extending from the chest drainage device, preventing the fluid collection container from pivoting.

Figure 12A:
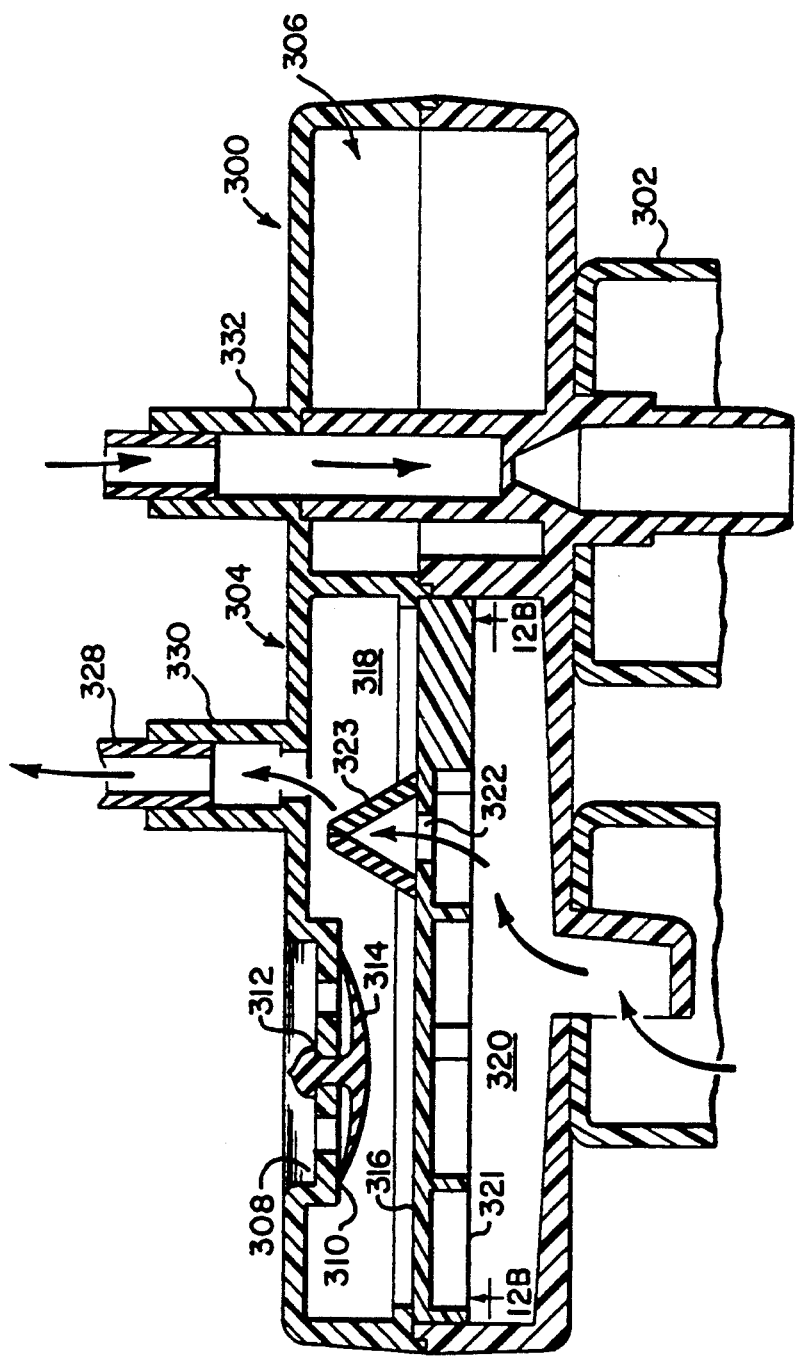
FIG. 12A is a diagramatic sectional illustration of a vacuum limiter mounted to the fluid collection container in accordance with the invention.
Figure 12B:
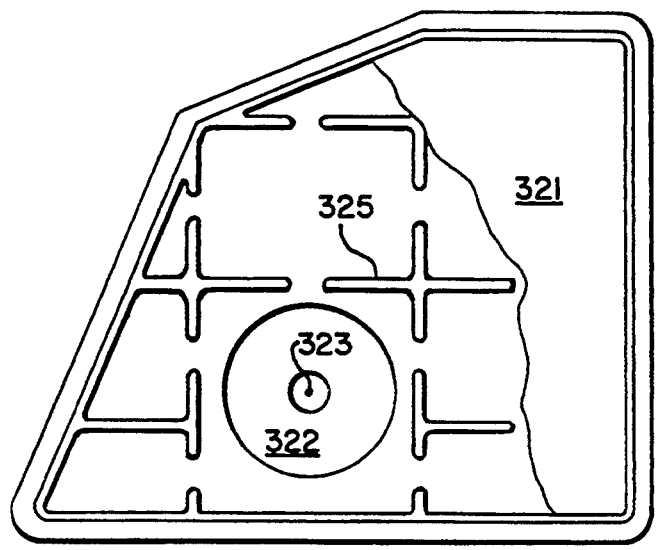
FIG. 12B is a sectional illustration along line 12B of FIG. 12A.

In FIGS. 12A-B, a vacuum limiter 300 limits (to within safe levels) the vacuum applied to the fluid collection container 302, and ultimately to the wound or cavity being drained, preventing trauma and excessive bleeding which may result from high vacuum conditions. The vacuum limiter 300 includes a housing having a suction chamber 304 and a fluid inlet chamber 306. An opening 308 extending through the top of the suction chamber 304 is fitted with a valve seat frame 310 and a collar 312 for holding the stem of an umbrella valve 314. A divider plate 316 separates the suction chamber 304 between a suction source side 318 and a fluid collection container side 320. A gas fluid outlet 322 extends from the collection container side 320 through the divider plate 316 and is fitted with a resilient one-way duckbill valve 323 which permits gas flow only from the fluid collection container side 320 to the suction side 318 and not in the reverse direction. A hydrophobic filter 321 is supported by the dividing plate 316 relative to the gas fluid outlet 322 of the fluid collection container. A grid-shaped baffle 325 extends from the divider plate 316 and provides a flow path for the evacuating gases to the outlet 322. The hydrophobic filter 321 allows air and other body gases 320 but not liquids, to pass from the fluid collection side 320 to the suction side 318. The hydrophobic filter 321 prevents blood from exhausting into the suction source even if the container is accidentally tipped over.

A suction inlet 330 is connected by a tube 328 to a source of suction such as the wall outlet of a hospital suction system. A fluid inlet 332 then is connected to a tube 333 in communication with the wound or cavity being drained, for example, a drain tube with a distal end emplaced in the pleural cavity. Gas and fluids from the pleural cavity are drawn by the negative pressure through the drain tube 333 and into the fluid collection container interior. When the negative pressure in the suction chamber 304 exceeds a predetermined minimum value, the umbrella valve 314 cracks open and admits atmospheric air into the suction side of the suction chamber which is drawn by the vacuum through the suction port 330. The umbrella valve 314 remains open until the level of suction from the hospital vacuum source returns within the predetermined safe range.

Figure 13A:
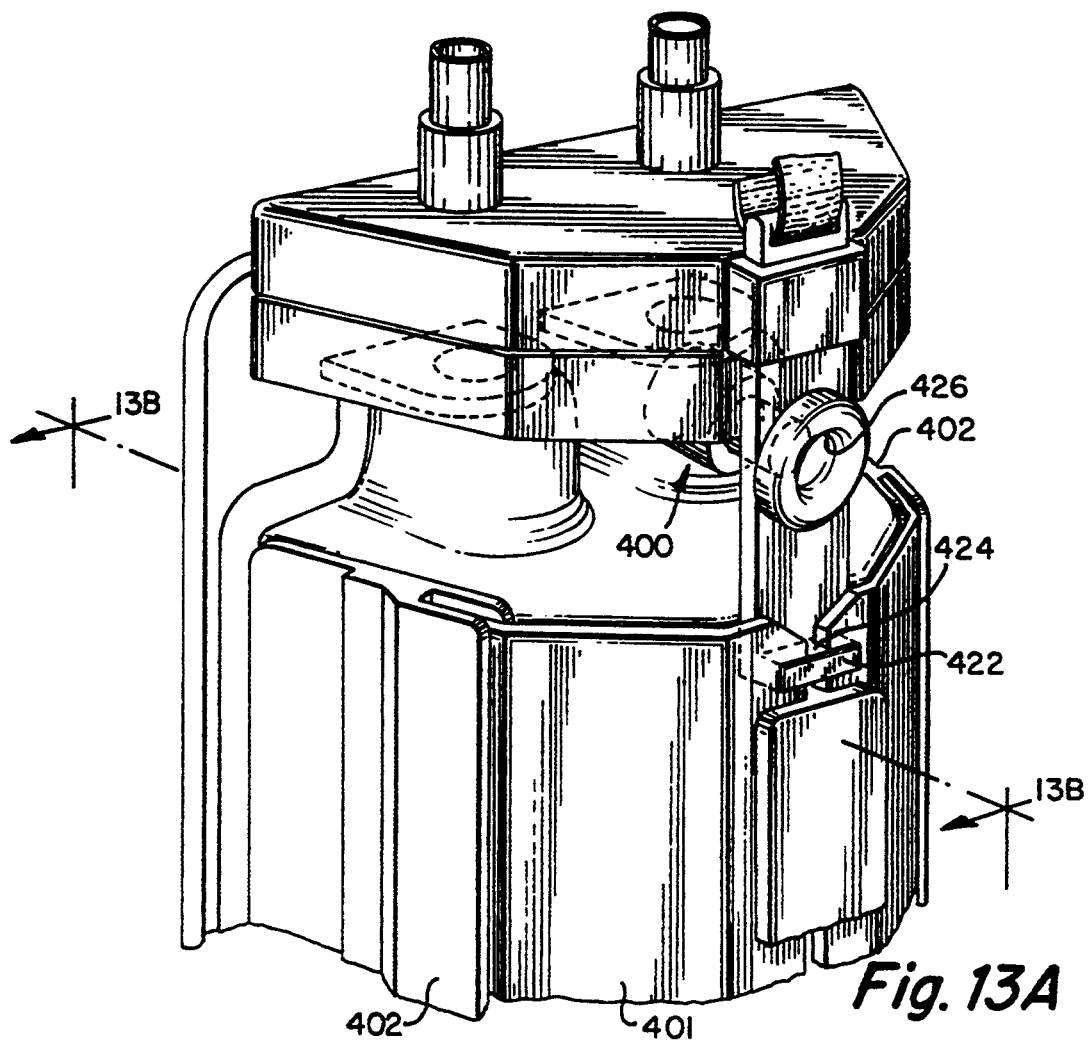
FIG. 13A is an illustration of a vacuum limiter with a venting system for dissipating the effect of the vacuum in the container.
Figure 13B:
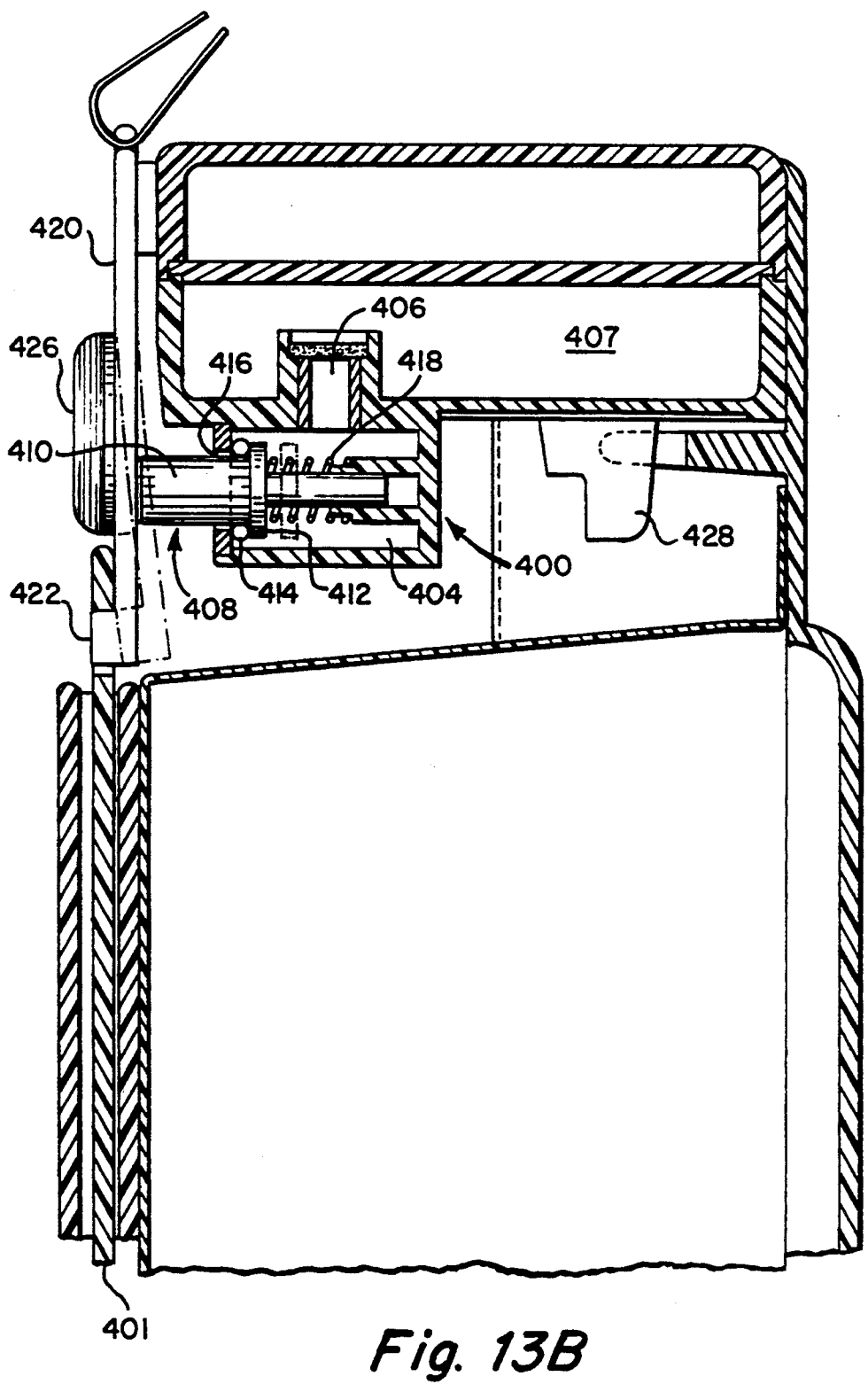
FIG. 13B is a sectional illustration of the vacuum limiter with a venting system along line 13B of FIG. 13A.

A venting system 400 is illustrated in FIGS. 13A-B which selectively admits atmospheric air into the container interior, dissipating the container vacuum and facilitating detachment of the stent 401 from the stent engaging panels 402. The venting system 400 includes a venting chamber 404 with a port 406 which is in communication with the fluid collection container side 407 of the vacuum limiter suction chamber. A valve 408 having a stem 410 and a head 412 is slidably mounted in the chamber. An O-ring 414 together with the face of the valve head 412 seals the opening 416 to the venting chamber when the valve 408 is in the normally closed position. A spring 418 biases the valve head 412 against the vent housing surrounding the opening 416. A lever 420 extends downwardly from the vacuum limiter which has a male projection 422 for engaging a notch 424 in the stent. Selective depression of the button 426 pivots the lever 420 against the valve stem 410, reciprocally advancing the valve head 412 away from the wall of the vent chamber. In this open position, atmospheric air bleeds through the grooves in the valve stem 414, into the vent chamber 404, through the vent port 406, and into the fluid collection side 407 of the suction chamber. The atmospheric air then flows through the suction inlet 428 and into the collection bag, diminishing the negative pressures operating therein.

The present invention thus provides a collapsible and expandable container for collecting fluids under the influence of a vacuum. To prevent the pliable container walls from collapsing, a rigid stent is interlocked to a series of rigid stent engaging panels spaced about the surface of the container. Collapse of the bag walls, which facilitates reinfusion of the collected liquids, is permitted by the quick and easy detachment of the stent.

It should be understood that the foregoing description of the invention is intended merely to be illustrative thereof and that other equivalents, embodiments and modifications of the invention may be apparent to those skilled in the art.

What is claimed is:

1. A fluid collection container, comprising:
   a collection bag having a variable volume interior and including a non-collapsible, rigid front wall and a flexible rear wall which is collapsible and distendible relative to said non-collapsible, rigid front wall;
   a plurality of stent engaging members attached to spaced about said flexible rear wall; a rigid stent releasably engageable to said plurality of spaced stent engaging members to maintain said flexible rear wall in a distended position relative to said rigid front wall;
   said collapsible collection bag including a first port in communication with said variable volume interior and having a proximal end which is connectable to a source of suction, and a second port in communication with said variable volume interior and having a proximal end which is connectable to a tube for conducting the fluid to be collected.

2. The fluid collection container recited in claim 1 wherein said non-collapsible, rigid front wall includes a rear surface which opposes said flexible rear wall, said rear surface having at least one rigid projection for preventing the rear wall from collapsing directly against said rear surface.

3. The fluid collection container recited in claim 2 wherein said at least one rigid projection includes a plurality of spaced rigid rib-shaped projections.

4. The fluid collection container recited in claim 3 wherein said plurality of spaced rigid rib-shaped projections extend parallel to a longitudinal axis of said non-collapsible, rigid front wall.

5. The fluid collection container recited in claim 1 further including a reinfusion port which is supported by said non-collapsible, rigid front wall and wherein said collection bag further includes a bottom wall having a portion thereof defining a reinfusion channel in communication with said reinfusion port.

6. The fluid collection container recited in claim 5 wherein a reinfusion tube is connected to said reinfusion port and said non-collapsible, rigid front wall further includes a slot adapted to hold said reinfusion tube.

7. The fluid collection container recited in claim 5 wherein said non-collapsible, rigid front wall includes a rear surface opposing said flexible rear wall and a pair of spaced rigid rib-shaped projections extending along said rear surface which form a pathway to said reinfusion channel.

8. The fluid collection container recited in claim 1 further comprising a flange extending from said front wall, said flange having a first opening adapted to receive said first port and a second opening adapted to receive said second port.

9. The fluid collection container recited in claim 1 wherein said flexible rear wall includes an open-ended flexible fluid collection bag, a marginal portion of said flexible fluid collection bag defining said open end being connected to said non-collapsible, rigid front wall.

10. The fluid collection container recited in claim 1 wherein said non-collapsible, rigid front wall further includes a non-collapsible, rigid belly projecting away from said flexible rear wall and defining a portion of said variable volume interior.

11. The fluid collection container recited in claim 1 wherein said non-collapsible, rigid front wall is transparent.

12. The fluid collection container recited in claim 11 wherein said transparent non-collapsible, rigid front wall further includes indicia for indicating the volume of the liquids accumulating in said variable volume interior.

13. A fluid collection container, comprising:
a collection bag having a variable volume interior and including a non-collapsible, rigid front wall and a flexible rear wall which is collapsible and distendible relative to said non-collapsible, rigid front wall;
a plurality of stent engaging members spaced about and attached to said collapsible and distendible rear wall so that all of said plurality of stent engaging members are arranged side by side rather than overlaying each other, and with adjacent edges being contiguous when said rear wall is collapsed;
a rigid stent releasably engageable to said plurality of spaced stent engaging members to maintain said collapsible and distendible rear wall in a distended position relative to said rigid front wall;
said collapsible collection bag including a first port in communication with said variable volume interior and having a proximal end which is connectable to a source of suction, and a second port in communication with said variable volume interior and having a proximal end which is connectable to a tube for conducting the fluid to be collected.

14. The fluid collection container recited in claim 13 wherein each of said plurality of spaced stent engaging members includes a flat surface attached to said collapsible and distendible rear wall.

15. A fluid collection container, comprising:
a collection bag having a variable volume interior and including a non-collapsible, rigid front wall and a plurality of collapsible and distendible walls;
a plurality of stent connecting members connected to at least some of said plurality of collapsible and distendible walls, at least one of said plurality of stent connecting members having a perimeter substantially coextensive with the perimeter of a collapsible and distendible wall to which it is connected;
a rigid stent releasably engageable to said plurality of stent connecting members to maintain said plurality of collapsible and distendible walls in a distended position relative to said rigid front wall;
said collection bag including a first port in communication with said variable volume interior and having a proximal end which is connectable to a source of suction, and a second port in communication with said variable volume interior and having a proximal end which is connectable to a tube for conducting the fluid to be collected.

16. The fluid collection container recited in claim 15 wherein said at least one of said plurality of stent connecting members includes a rigid, elongated flat panel.

17. The fluid collection container recited in claim 15 wherein alternating of said plurality of collapsible and distendible walls are each connected to at least one of said plurality of stent connecting members.

18. The fluid collection container recited in claim 15 wherein said plurality of collapsible and distendible walls, when in a fully distended position, includes a pair of spaced converging side walls, a second pair of spaced converging side walls extending from said first pair, and a rear wall extending between said second pair of spaced converging side walls.

19. The fluid collection container recited in claim 18 wherein said rear wall is parallel with said front wall of said collection bag when said plurality of collapsible and distendible side walls are fully distended.

20. The fluid collection container recited in claim 18 wherein said rear wall has a smaller perimeter than either of said first pair of converging side walls.

21. The fluid collection container recited in claim 18 wherein said at least one of said plurality of collapsible and distendible walls includes said first pair of converging side walls and said rear wall.

22. The fluid collection container recited in claim 15 wherein said at least one of said plurality of stent connecting members includes all of said plurality of stent connecting members.

23. A fluid collection container, comprising:
a collection bag having a variable volume interior and including a non-collapsible, rigid front wall, a pair of side walls and a rear wall extending between said pair of side walls, said pair of side walls and rear wall being collapsible and distendible relative to said non-collapsible, rigid front wall;
a pair of flat members respectively connected to said pair of side walls, each of said flat members having a perimeter substantially coextensive with the perimeter of said respectively connected side wall and including an elongated flange having an elongated stent-receiving space;

a center flat member connected to said rear wall and including a projecting flange extending away from said rear wall;

a rigid stent releasably engageable to said pair of flat members and said central flat member to maintain said pair of side walls and said rear wall in a distended position, said elongated rigid stent including a central portion having a slot adapted to slidably receive said projecting flange and a pair of end portions diverging from said central portion adapted to be slidably received within said elongated stent-receiving space;

said collapsible collection bag including a first port in communication with said variable volume interior and having a proximal end which is connectable to a source of suction, and a second port in communication with said variable volume interior and having a proximal end which is connectable to tube for conducting the fluid to be collected.

24. The fluid collection container recited in claim 23 further including a pair of opposed lateral portions extending respectively between said front wall and said pair of side walls wherein each of said pair of side walls diverges from said opposed lateral portions towards said rear wall.

25. The fluid collection container recited in claim 24 wherein said opposed lateral portions extend perpendicularly from said front wall.

26. The fluid collection container recited in claim 25 wherein said rear wall includes a central region and a pair of lateral regions diverging from opposite sides of said central region, said central region being parallel with said rigid front wall when said collection bag is fully distended and wherein said center flat member is attached to said central region and has a perimeter substantially coextensive with said central region.

27. The fluid collection container recited in claim 26 wherein said elongated rigid stent further includes a pair of lateral portions diverging respectively from opposite sides of said central portion and extending to said diverging end portions.

28. A fluid collection container, comprising:

a collection bag having a variable volume interior and including a non-collapsible, rigid front wall and a flexible rear wall which is collapsible and distendible relative to said non-collapsible, rigid front wall, said flexible rear wall including an upper portion, a lower portion and an intermediate portion;

a plurality of stent engaging members attached to and spaced about said flexible rear wall;

a rigid stent releasably engaged to said plurality of stent engaging members and extending across said intermediate portion of said rear wall between said plurality of stent engaging members for maintaining said flexible rear wall in a distended position relative to said rigid front wall; said collapsible collection bag including a first port in communication with said variable volume interior and having a proximal end which is connectable to a tube for conducting the fluid to be collected and a second port in communication with said variable volume interior and having a proximal end which is connectable to a source of suction.

* * * * *